United States Patent
Song

(10) Patent No.: US 11,344,043 B2
(45) Date of Patent: May 31, 2022

(54) METHOD FOR PRODUCING FERMENTED COFFEE USING ENTERIC BACTERIA OF KOPI LUWAK

(71) Applicant: Young Youb Song, Seongnam-si (KR)

(72) Inventor: Young Youb Song, Seongnam-si (KR)

(*) Notice: Subject to any disclaimer, the term of this patent is extended or adjusted under 35 U.S.C. 154(b) by 417 days.

(21) Appl. No.: 16/498,471

(22) PCT Filed: Apr. 2, 2018

(86) PCT No.: PCT/KR2018/003874
§ 371 (c)(1),
(2) Date: Sep. 27, 2019

(87) PCT Pub. No.: WO2018/182389
PCT Pub. Date: Oct. 4, 2018

(65) Prior Publication Data
US 2021/0169098 A1    Jun. 10, 2021

(30) Foreign Application Priority Data

Mar. 31, 2017   (KR) .................. 10-2017-0042213

(51) Int. Cl.
*A23F 5/20* (2006.01)
*A23F 5/10* (2006.01)
*C12N 1/20* (2006.01)

(52) U.S. Cl.
CPC .............. *A23F 5/204* (2013.01); *A23F 5/105* (2013.01); *C12N 1/20* (2013.01); *A23Y 2220/67* (2013.01)

(58) Field of Classification Search
CPC ............ A23F 5/105; A23F 5/204; C12N 1/20
See application file for complete search history.

(56) References Cited

U.S. PATENT DOCUMENTS

2009/0220645 A1* 9/2009 Martinez ................... A23F 5/02
426/45
2010/0239711 A1* 9/2010 Li ............................. A23F 5/02
426/45

FOREIGN PATENT DOCUMENTS

| KR | 10-2015-0061986 A | | 6/2015 |
| KR | 10-2016-0063628 A | | 6/2016 |
| KR | 10-2016-0063645 A | | 6/2016 |
| KR | 10-2017-0028768 A | | 3/2017 |
| KR | 20170032636 | * | 3/2017 |

OTHER PUBLICATIONS

English Translation for KR20170032636 published Mar. 2017.*

* cited by examiner

*Primary Examiner* — Anthony J Weier
(74) *Attorney, Agent, or Firm* — KORUS Patent, LLC; Seong Il Jeong

(57) ABSTRACT

The present invention relates to a method for producing fermented and vacuum-treated coffee using Kopi Luwak enterobacteria, in which the coffee contains a low concentration of caffeine and a high concentration of γ-aminobutyric acid (GABA). According to the present invention, the fermented and vacuum-treated coffee produced using Kopi Luwak enterobacteria according to the present invention has advantages in that it is produced by rapid fermentation, uniquely smells like caramel, chocolate, grass, etc., unlike unfermented green coffee beans, and has a reduced bitter taste and a deep and heavy taste with an appropriate sour taste.

1 Claim, 1 Drawing Sheet

METHOD FOR PRODUCING FERMENTED COFFEE USING ENTERIC BACTERIA OF KOPI LUWAK

TECHNICAL FIELD

The present invention relates to a method for producing fermented coffee using Kopi Luwak enterobacteria, and more particularly to a method for producing fermented coffee using Kopi Luwak enterobacteria, by which fermented coffee containing a low concentration of caffeine and a high concentration of γ-aminobutyric acid (GABA) is produced by fermenting green coffee beans using Kopi Luwak enterobacteria, followed by vacuum treatment.

BACKGROUND ART

Coffee is a beverage that is enjoyed by one third of the world's population and consumed more than any other beverage. The content of caffeine is 1.3% in roasted coffee and 0.8% in instant coffee. Caffeine stimulates the central nervous system, has diuretic action, and also has smooth muscle relaxation action and peripheral blood vessel dilation action. In addition, it also has analgesic action due to its prostaglandin synthesis inhibitory action. Thus, it is effective against bronchial asthma, migraine, neuralgia, etc.

Various caffeine removal methods are known in the art. The most common technology is a method including: swelling green coffee beans with water; extracting caffeine from the swollen green coffee beans using an organic solvent or a caffeine-free solution for solubilizing the green coffee beans; bringing the resulting solution into contact with a solvent; and removing caffeine from the solution. In either case, at least portion of the solvent typically comes into contact with the green coffee beans, and a very small amount of the solvent remains in the green coffee beans. The most useful solvents are halogenated hydrocarbons, but it is preferred that such solvents are not used so that even a trace amount of solvent does not remain in coffee. As an improvement over the caffeine extraction method utilizing the solvent, there is a method of extracting caffeine from green coffee beans using supercritical carbon dioxide. This technology is disclosed in U.S. Pat. No. 4,260,639, etc., and is a process of absorbing caffeine from supercritical carbon dioxide containing caffeine. However, this process also requires expensive and complex processes and equipment, and thus a suitable caffeine removal method capable of replacing it is required.

γ-Aminobutyric acid (GABA), a non-protein amino acid, is a substance which has a molecular weight of 103.12 and a melting point of 203° C., is stable against heat, and is highly soluble in water. The mechanism of production of GABA is elucidated in more detail in microorganisms than in animals or plants. In the second half of the microbial growth process, intracellular and extracellular hydrogen ion ($H^+$) concentrations are unbalanced due to excessive accumulation of extracellular metabolites, and GABA is produced by an action for overcoming this unbalance. Specifically, when glutamate present outside cells enters cells, that is, when the carboxyl group of glutamate enters cells by glutamate that is present inside and outside cells, the carboxyl group of glutamate is substituted with hydrogen ions ($H^+$) accumulated in the cells to produce carbon dioxide ($CO_2$), thereby exhausting intracellular hydrogen ions ($H^+$), and GABA is produced in this process. That is, it has been reported that a GAD enzyme that is involved in this reaction has acid stress resistance at a pH between 4.2 and 4.7, and coenzymes for this enzyme include 5'-pyridoxal phosphate (PLP).

The above-described GABA is known to be present in the brains of animals and play an important role as a neurotransmitter in the central nervous system, and has been recognized to have effects on stroke prevention, dementia prevention, mental attention strengthening, memory enhancement, insomnia alleviation, etc.

Regarding one Japanese study on the efficacy of GABA, a study conducted by examining menopausal disorders and elderly psychiatric disorders after oral administration of rice embryos having GABA accumulated therein reported that daily ingestion of 26.5 mg of GABA healed about 75% of mental illnesses, such as headaches or depression, or various menopausal disorders.

Currently, there are two types of coffee: green bean coffee which is used after roasting and grinding; and instant coffee obtained by spray-drying and freeze-drying coffee extracts. Green bean coffee contains small amounts of active ingredients because it is leached in small amounts during a leaching process, and instant coffee is leached in large amounts, but active ingredients thereof are not decomposed, and thus are not absorbed in large amounts.

Commercially available soluble coffee is generally produced by solubilizing highly roasted and ground coffee beans through a stepwise heat treatment process consisting of a combination of a wetting step, an extraction step and a hydrolysis step. Off-flavor is caused due to a very high temperature required to perform thermal hydrolysis, and this process requires an enormous expense and investment. Various methods based on enzymatic treatment have been reported which use carbohydrase to improve product quality and increase process economics (Japanese Patent No. JP-74012710, and U.S. Pat. Nos. 4,983,408, 4,133,207 and 4,461,648). These methods have several advantages, but pretreatment of coffee grounds, such as dry grinding, is inefficient, and hence the overall yield is lower than the optimum yield. In addition, any countermeasures for separating the enzyme from the final product or reusing the enzyme are not provided.

Regarding fermented coffees, commercially available coffees include monsooned coffee and Kopi Luwak coffee. Monsooned coffee refers to coffee that has been constantly exposed to wet monsoon winds in open warehouses.

Currently, the most common monsooned coffee is Indian Malabar coffee. Malabar coffee is usually produced by fermentation at the bottom of a warehouse on the west coast of Ando during the monsoon season while being wet by about 12 to 16 weeks of exposure to winds coming from the Arabian Sea. The biggest feature of this coffee is its reduced acidity. Monsooned coffee is not high-quality specialty coffee, but it is distributed in Europe because of its unique taste. However, Monsooned coffee is an unusual coffee which is enjoyed by a small number of lovers due to its unique taste.

Kopi Luwak is also called Alamid. 'Luwak' is Indonesian, and 'Alamid' is Filipino, and both mean the civet. The two differ only in name and have the same taste and aroma. A process for producing Kopi Luwak is performed by a fermentation process using wild civets. Wild civets, which mainly inhabit Southeast Asia, use their excellent sense of smell to pick coffee fruits which are ripe, delicious palm nuts. The flesh is digested, and the non-digested coffee fruit seeds are excreted. At this time, saliva and gastric juice of the civets are mixed with the seeds, and the seeds are fermented in the digestive system, thereby reducing the characteristic bitter taste of coffee and giving a unique taste and aroma. The coffee beans of our dreams are in the excrement of civets. The reason why Kopi Luwak is produced in small amounts is because of this process in which it is produced by the civet. At harvest time, nearby residents collect the civet excrement before sunrise. Then, the coffee beans are picked from the civet excrement, washed clean and dried well in the sun. The parchment of the dried coffee beans is removed, and then the coffee beans are subjected to a roasting process, thereby providing a green coffee bean product. However, Kopi Luwak is sold at a high price of 70,000 Won (Korean currency), and hence it is hard for the public to enjoy Kopi Luwak on a daily basis. Therefore, there is a need to develop and popularize fermented coffee which has a reduced bitter taste of coffee and gives a unique taste and aroma.

Accordingly, the present inventor has made extensive research efforts to overcome the above-described problems occurring in the prior art, and as a result, has found that, when Kopi Luwak is produced by fermenting green coffee beans using Kopi Luwak enterobacteria, followed by vacuum treatment, it is possible to produce Kopi Luwak which has a low caffeine concentration, contains a high content of γ-aminobutyric acid (GABA) from green coffee beans themselves, has a reduced bitter taste of coffee, and gives a unique taste and aroma, thereby completing the present invention.

DISCLOSURE

Technical Problem

Accordingly, a main object of the present invention is to provide a method for producing fermented coffee using Kopi Luwak enterobacteria, in which fermented coffee contains a high content of γ-aminobutyric acid (GABA), has a reduced caffeine concentration, has a reduced bitter taste of coffee, and gives a unique taste and aroma.

Technical Solution

A method for producing fermented coffee using Kopi Luwak enterobacteria according to one embodiment of the present invention includes: a starter culture step of collecting Kopi Luwak excreted from civets which picked green coffee beans, placing ⅓ 9% saline and ⅔ green Kopi Luwak beans in a beaker, sealing the beaker with filter paper, and then incubating the beaker in an incubator at 18° C. for 4 to 5 days, thereby obtaining a *Lactobacillus* starter culture including Kopi Luwak *Bacillus*, Kopi Luwak *Aspergillus*, Kopi Luwak *Lactobacillus*, and Kopi Luwak yeast; a fermentation step of washing coffee beans, obtained by removing parchments from dried green coffee beans, with water, and inoculating the washed coffee beans with at least 3% (v/v) of the *Lactobacillus* starter culture including Kopi Luwak *Bacillus*, Kopi Luwak *Aspergillus*, Kopi Luwak *Lactobacillus* and Kopi Luwak yeast, cultured in the starter culture step, followed by fermentation in an incubator at 37° C. for 20 hours; and a vacuum treatment step of placing the Luwak coffee, fermented in the fermentation step, in a vacuum chamber, followed by vacuum treatment at $10^{-2}$ mmgH and 25° C. for 4 hours.

Advantageous Effects

According to the method of the present invention, it is possible to produce a Luwak coffee which smells like caramel, chocolate, grass, etc., has a reduced bitter taste, has a deep and heavy taste with an appropriate sour taste, contains a high content of γ-aminobutyric acid (GABA), and has a reduced caffeine concentration.

BEST MODE

Figure 1:
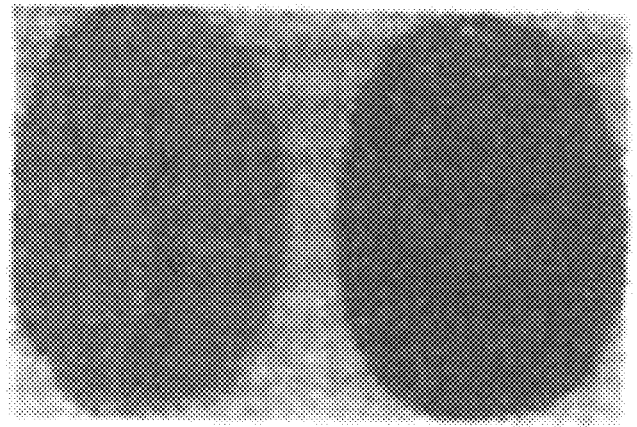
FIG. 1 is a view showing an Arabica coffee and a coffee bean fermented using Kopi Luwak enterobacteria.

The present invention relates to a method for producing fermented coffee using Kopi Luwak enterobacteria. The method may include: a starter culture step of collecting Kopi Luwak excreted from civets which picked green coffee beans, placing ⅓ 9% saline and ⅔ green Kopi Luwak beans in a beaker, sealing the beaker with filter paper, and then incubating the beaker in an incubator at 18° C. for 4 to 5 days, thereby obtaining a *Lactobacillus* starter culture including Kopi Luwak *Bacillus*, Kopi Luwak *Aspergillus*, Kopi Luwak *Lactobacillus*, and Kopi Luwak yeast; a step of centrifuging the starter culture at 500 to 1500 rpm for 5 to 15 minutes, 7000 to 12000 rpm for 5 to 15 minutes, and 20000 to 50000 rpm for 20 to 40 minutes, thereby separating each of *Bacillus subtilis* which is a member of the Kopi Luwak *Bacillus*, *Aspergillus tamarii* which is a member of the Kopi Luwak *Aspergillus*, *Lactobacillus plantarum* which is a member of the Kopi Luwak *Lactobacillus*, and *Zygosaccharomyces major* which is a member of the Kopi Luwak yeast; a fermentation step of washing coffee beans, obtained by removing parchments from dried green coffee beans, with water, swelling the washed beans, drying the swollen coffee beans with hot air, keeping the dried coffee beans at a humidity of 50%, and then inoculating the coffee beans with a controlled amount of each of the separated *Bacillus subtilis*, *Aspergillus tamarii*, *Lactobacillus plantarum* and *Zygosaccharomyces major*, followed by fermentation in an incubator at 37° C. for 20 hours; and a vacuum treatment step of placing the Luwak coffee, fermented in the fermentation step, in a vacuum chamber, followed by vacuum treatment at $10^{-2}$ mmgH and 25° C. for 4 hours.

MODE FOR INVENTION

Hereinafter, preferred embodiments of the present invention will be described in detail with reference to the accompanying drawings.

The term 'Kopi Luwak enterobacteria' as used in the present invention refers to bacteria that are found during fermentation of green Kopi Luwak beans. Most of the Kopi Luwak enterobacteria are composed of Kopi Luwak *Bacillus*, Kopi Luwak *Aspergillus*, Kopi Luwak *Lactobacillus*, and Kopi Luwak yeast.

Starter Culture Step

Kopi Luwak excreted from civets which picked green coffee beans from coffee tree fruits is collected, and ⅓ 9% saline and ⅔ Kopi Luwak are placed in a beaker. The beaker is sealed with filter paper, and then incubated in an incubator at 15 to 21° C., preferably 18° C., for 4 to 5 days, thereby extracting starters (*Lactobacillus*), that is, Kopi Luwak *Bacillus*, Kopi Luwak *Aspergillus*, Kopi Luwak *Lactobacillus*, and Kopi Luwak yeast.

Here, the Kopi Luwak *Bacillus* may be any one or more selected from among *Bacillus subtilis* and *Bacillus natto*.

Moreover, the Kopi Luwak *Aspergillus* may be any one or more selected from among *Aspergilus oryzae*, *Aspergilus sojae* and *Aspergillus tamarii*.

Furthermore, the Kopi Luwak *Lactobacillus* may be any one or more selected from among *Leusonost mesenteroides*, *Lactobacillus plantarum*, *Lactobacillus brevis*, *Leuconostoc gastcomitaum*, *Leuconostoc lactis*, *Lactobacillus acidophilus*, *Bifidobacterium longum*, and *Streptococctus thermophilus*.

In addition, the Kopi Luwak yeast may be any one or more selected from among *Zygosaccharomyces major* and *Saccharomyces cerevisiae*.

TABLE 1

| 9% Saline | Excreted Kopi Luwak green beans | Room temperature (18° C.) |
|---|---|---|
| 1/3 | 2/3 | 4 to 5 days |

Starter Separation Step

The resulting starter culture is placed in a centrifuge and centrifuged at 500 to 1500 rpm for 5 to 15 minutes, 7000 to 12000 rpm for 5 to 15 minutes, and 20000 to 50000 rpm for 20 to 40 minutes, thereby separating each of *Bacillus subtilis* which is a member of the Kopi Luwak *Bacillus*, *Aspergillus tamarii* which is a member of the Kopi Luwak *Aspergillus*, *Lactobacillus plantarum* which is a member of the Kopi Luwak *Lactobacillus*, and *Zygosaccharomyces major* which is a member of the Kopi Luwak yeast. This starter separation step is a process of separating *Bacillus subtilis*, *Aspergillus tamarii*, *Lactobacillus plantarum* and *Zygosaccharomyces major*, which make the taste of fermented coffee closest to the taste of actual Kopi Luwak coffee, from the *Lactobacillus* starter culture including Kopi Luwak *Bacillus*, Kopi Luwak *Aspergillus*, Kopi Luwak *Lactobacillus*, and Kopi Luwak yeast.

TABLE 2

| | Centrifugation speed (rpm)/time | | |
|---|---|---|---|
| | 800 rpm/ 10 min | 10000 rpm/ 10 min | 25000 rpm/ 30 min |
| Starter %: mixing and culture depending on taste and aroma in the range of 1 to 10 mg | Nuclear fraction | Upper layer yeast Lower layer *Lactobacillus* | Upper layer *Aspergillus* Lower layer *Bacillus* |

Fermentation Step

Green coffee beans are washed with water, and then mixed with about 0.5 to 2% or 0.05 to 0.2% sterile medium (2.0 mg/l MRS). Then, the resulting coffee beans are inoculated with 3% (v/v) or more of the starter culture extracted in the above-described starter culture step. Next, the coffee beans are fermented in an incubator at 35 to 40° C. for 18 to 21 hours. Specifically, green coffee beans obtained by removing parchments from dried green coffee beans are washed with drinking water, and then swollen. Then, the green coffee beans are dried with hot air at 65 to 75° C. and kept at a humidity of 40 to 60%. Then, at a temperature of 35 to 40° C., the coffee beans are inoculated directly with the separated *Bacillus subtilis*, *Aspergillus tamarii*, *Lactobacillus plantarum* and *Zygosaccharomyces major* mixed with medium (2.0 mg/l). Next, the coffee beans are fermented in an incubator at 35 to 40° C. for 18 to 21 hours.

TABLE 3

| Coffee beans | Washing of coffee beans with drinking water | Coffee bean humidity % | Kopi Luwak enterobacteria: | Incubator temperature (° C.) | Time |
|---|---|---|---|---|---|
| | Hot air drying at 70° C. | 50 | *Bacillus*, *Aspergillus*, *Lactobacillus*, yeast Medium: MRS + 2.0 mg/l | 37 | 20 hours |

Vacuum Treatment Step

The Luwak coffee fermented in the fermentation step is placed in a vacuum chamber and vacuum-treated at $10^{-2}$ mmgH and 25° C. for 4 hours.

TABLE 4

| Vacuum level | Time | Temperature (° C.) | Swelling (%) of coffee beans |
|---|---|---|---|
| $10^{-2}$ mmgH | 4 hours | 25 | 10 |

Figure 2:
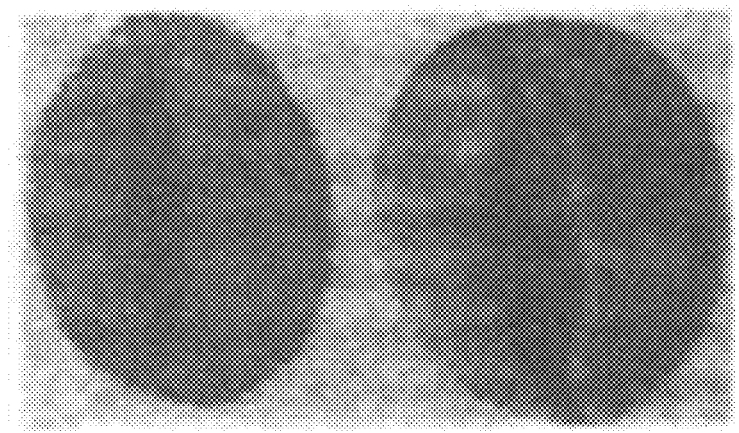
FIG. 2 is a view showing a Robusta coffee bean a coffee bean fermented using Kopi Luwak enterobacteria.

FIGS. 1 and 2 are views showing an Arabica coffee bean, a Robusta coffee bean, and coffee beans fermented using Kopi Luwak enterobacteria according to the present invention. As can be seen therein, the coffee beans were expanded and increased in size.

TABLE 5

| Coffee | Taste | Aroma | Assessment |
|---|---|---|---|
| Indonesian | 5 | 6 | 5 |
| Fermented Luwak coffee | 7 | 8 | 7 |
| Fermented and vacuum-treated Luwak coffee | 9 | 9 | 9 |

The produced fermented coffee (Luwak coffee) was analyzed comparatively with the coffee before fermentation.

[Table 6] Analysis Results

A comparison of the coffee components after fermentation with those before fermentation indicated that the caffeine content of the fermented coffee decreased to about 12% of that of the coffee before fermentation (0.15 g/100 g), and the γ-aminobutyric acid (GABA) concentration of the fermented coffee increased at least 5-fold compared to that of the coffee before fermentation. In addition, the caffeine content of the coffee obtained by vacuum treatment after fermentation decreased to about 8% of that of the coffee before fermentation (0.1 g/100 g), and the γ-aminobutyric acid (GABA) concentration thereof increased at least 10-fold compared to that of the coffee before fermentation.

TABLE 6

| Components | Caffeine content of green coffee beans | GABA concentration of green coffee beans |
|---|---|---|
| Coffee for fermentation | 1.2 g/100 g | 0.1 mg/100 g |
| Fermented coffee | 0.15 g/100 g | 5-fold |
| Fermented and vacuum-treated coffee | 0.1 g/100 g | 10-fold |

'Low-concentration caffeine' in the present invention means that the green coffee beans after fermentation have a caffeine content that decreased to at least 12.6% (preferably about 8%) of that of the green coffee beans before fermentation.

Meanwhile, although the method used to sterilize the green coffee beans in the present invention may be any sterilization method known in the art, the green coffee beans may also be washed with water, immersed, and then taken out and inoculated with the starter culture.

In addition, in order to ferment the green coffee beans with Kopi Luwak *Lactobacillus*, liquid-state fermentation should be performed, and medium components may also be added for rapid growth of the *Lactobacillus*.

Substances that may be added together with the green coffee beans to the fermentation medium for culture of the Kopi Luwak *Lactobacillus* of the present invention may be any substances known in the art, which are generally added for culture of Kopi Luwak *Lactobacillus*. However, it is generally preferred to add water in an amount equal to 2 to 3 times the weight of the green coffee beans, carbohydrates such as glucose, refined sugar and dietary fiber, yeast extract, and proteins such as peptone, together with the green coffee beans.

In the present invention, the *Lactobacillus* may be any one or more selected from among *Leusonost mesenteroides, Lactobacillus plantarum, Lactobacillus brevis, Leuconostoc gastcomitaum, Leuconostoc lactis, Lactobacillus acidophilus, Bifidobacterium longum*, and *Streptococctus thermophilus*.

When the green coffee beans are inoculated with Kopi Luwak *Bacillus*, Kopi Luwak *Aspergillus*, Kopi Luwak *Lactobacillus*, and Kopi Luwak yeast, which are Kopi Luwak enterobacteria, and are fermented and then vacuum-treated, as disclosed in the present invention, the effect of removing caffeine from the green coffee beans by fermentation and vacuum treatment can be obtained, and fermented and vacuum-treated coffee containing a high concentration of GABA can be produced. Thus, the fermented and vacuum-treated coffee can be greatly helpful in sound sleep.

The fermented coffee of the present invention can overcome the problems with existing coffee by containing a high content of GABA having a sound sleep effect and reducing the content of caffeine having a stimulant action. At the same time, according to the present invention, the green coffee beans are fermented after inoculation with the Kopi Luwak *Lactobacillus*, thereby providing a coffee which is helpful in sound sleep and has an improved taste and aroma without changing the taste and aroma. Therefore, the present invention can overcome the problems associated with quality deterioration, which occur in a conventional art in which caffeine coffee is produced using an organic solvent or soluble coffee is produced using an enzyme.

INDUSTRIAL APPLICABILITY

According to the method of the present invention, it is possible to produce a Luwak coffee which smells like caramel, chocolate, grass, etc., has a reduced bitter taste, has a deep and heavy taste with an appropriate sour taste, contains a high content of γ-aminobutyric acid (GABA), and has a reduced caffeine concentration.

The invention claimed is:

1. A method for producing fermented coffee using Kopi Luwak enterobacteria, the method comprising:
   a starter culture step of collecting Kopi Luwak excreted from civets which picked green coffee beans, placing ⅓ 9% saline and ⅔ green Kopi Luwak beans in a beaker, sealing the beaker with filter paper, and then incubating the beaker in an incubator at 18° C. for 4 to 5 days, thereby obtaining a *Lactobacillus* starter culture comprising Kopi Luwak *Bacillus*, Kopi Luwak *Aspergillus*, Kopi Luwak *Lactobacillus*, and Kopi Luwak yeast;
   a step of centrifuging the starter culture at 500 to 1500 rpm for 5 to 15 minutes, 7000 to 12000 rpm for 5 to 15 minutes, and 20000 to 50000 rpm for 20 to 40 minutes, thereby separating each of *Bacillus subtilis* which is a member of the Kopi Luwak *Bacillus, Aspergillus tamarii* which is a member of the Kopi Luwak *Aspergillus, Lactobacillus plantarum* which is a member of the Kopi Luwak *Lactobacillus*, and *Zygosaccharomyces major* which is a member of the Kopi Luwak yeast;
   a fermentation step of washing coffee beans, obtained by removing parchments from dried green coffee beans, with water, swelling the washed beans, drying the swollen coffee beans with hot air, keeping the dried coffee beans at a humidity of 50%, and then inoculating the coffee beans with a controlled amount of each of the separated *Bacillus subtilis, Aspergillus tamarii, Lactobacillus plantarum* and *Zygosaccharomyces major*, followed by fermentation in an incubator at 37° C. for 20 hours; and
   a vacuum treatment step of placing the Luwak coffee, fermented in the fermentation step, in a vacuum chamber, followed by vacuum treatment at $10^{-2}$ mmgH and 25° C. for 4 hours.

* * * * *